United States Patent [19]
Hughes

[11] Patent Number: 5,340,927
[45] Date of Patent: Aug. 23, 1994

[54] PROCESS FOR THE PREPARATION OF 2-DIAZO-3-TRISUBSTITUTED SILYLOXY 3-BUTENOATES

[75] Inventor: David L. Hughes, Old Bridge, N.J.

[73] Assignee: Merck & Co., Inc., Rahway, N.J.

[21] Appl. No.: 846,725

[22] Filed: Mar. 2, 1992

Related U.S. Application Data

[63] Continuation of Ser. No. 611,237, Nov. 9, 1990, abandoned, which is a continuation-in-part of Ser. No. 381,344, Jul. 18, 1989, abandoned.

[51] Int. Cl.$^5$ ............................................. C07C 245/18
[52] U.S. Cl. ........................................................ 534/558
[58] Field of Search ........................................... 534/558

[56] References Cited

U.S. PATENT DOCUMENTS

| | | | |
|---|---|---|---|
| 4,444,685 | 4/1984 | Amato et al. | 260/239 |
| 4,525,582 | 5/1985 | Amato et al. | 534/558 |
| 4,683,296 | 7/1987 | Ueda et al. | 539/558 |
| 5,071,966 | 12/1991 | Kan et al. | 534/558 |

FOREIGN PATENT DOCUMENTS

| | | |
|---|---|---|
| 0078026 | 5/1983 | European Pat. Off. . |
| 2136009A | 9/1984 | United Kingdom . |
| 2173801A | 10/1986 | United Kingdom . |
| 90/08149 | 7/1990 | World Int. Prop. O. . |

OTHER PUBLICATIONS

Ceazeau et al. *Tetrahedron*, 43: 2075–2088 (1987).
Karady et al. *J. Am. Chem. Soc.* 103: 6765–6767 (1981).
Reider et al. *Tetrahedron Lett.*, 23: 379–382 (1982).
Ueda et al., *Can. J. Chem.*, 62: 2936–2940 (1984) IV.

*Primary Examiner*—Shailendra Kumar
*Attorney, Agent, or Firm*—Billups, Richard C.; Mark R. Daniels

[57] ABSTRACT

A novel process for preparing 2-diazo-3-trisubstituted silyloxy-3-butenoates, synthons useful in the conversion of 3-substituted-4-acetoxy azetidinones and penicillin to thienamycin, imipenem and other carbapenem antibiotic compounds is provided, comprising the reaction of the appropriate diazo acetoacetate with the substituted silane, base and salt.

7 Claims, No Drawings

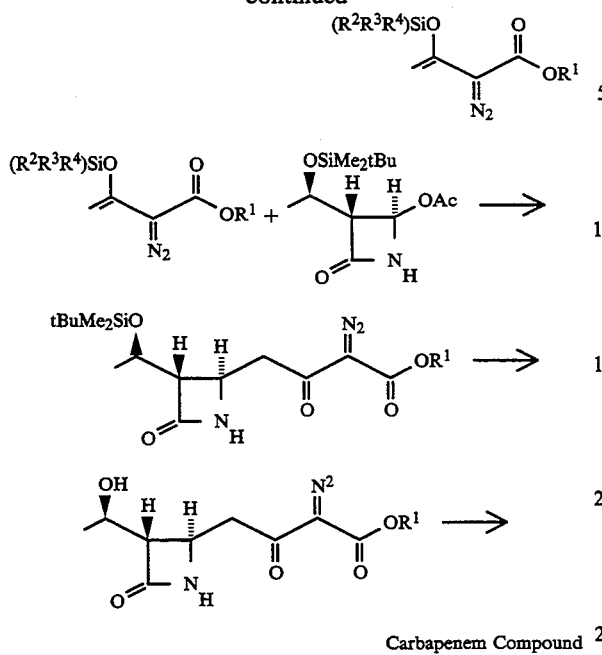

Carbapenem Compound

The commercially available methyl acetoacetate is treated with an equivalent molar amount of a suitably substituted alcohol in an inert atmosphere and the resulting acetoacetate treated with an equivalent of 4-dodecylbenzenesulfonyl azide and a catalytic amount of a base to produce the diazoacetoacetate.

The diazoacetoacetate is treated with an alkali metal iodide, a base and a triorganosilyl halide, preferably all in slight molar excess, in a suitable aprotic organic solvent in an inert atmosphere. The resulting silyloxy butenoate may be isolated or employed in solution in a reaction with a molar equivalent of the acetoxy azetidinone and a catalytic amount of zinc bromide and, when the reaction is complete, this mixture is treated with excess methanol and a catalytic amount of methane sulfonic acid. The final appended azetidinone is then isolated, for example by crystallization from the reaction solution.

A suitably substituted alcohol may be benzyl alcohol, p-methoxybenzyl alcohol, cinnamyl alcohol, allyl alcohol, p-bromobenzyl alcohol, o-nitrobenzyl alcohol, 2,4,6,-trimethylbenzyl alcohol, benzhydryl alcohol or trityl alcohol. The most preferred substituted alcohol is p-nitrobenzyl alcohol.

An inert atmosphere may be either nitrogen or argon gas.

The triorganosilyl halide may be any trialkyl ($C_1$–$C_4$ alkyl) silyl chloride (e.g. trimethyl silyl chloride, triethyl silyl chloride, triisopropyl silyl chloride or t-butyl dimethyl silyl chloride) or it may be t-butyl diphenyl silyl chloride, dimethyl phenyl silyl chloride, diphenyl methyl silyl chloride or (2,4,6- tri-t-butyl phenoxy) dimethyl silyl chloride or the corresponding silyl bromides of the above listed reagents. The most preferred silylating agent is trimethyl silyl chloride.

The alkali metal iodide may be sodium iodide, potassium iodide or cesium iodide.

A suitable aprotic organic solvent may be methylene chloride, tetrahydrofuran, carbon tetrachloride, dioxane, dimethoxyethane, diethyl ether, chloroform, an acetonitrile/toluene mixture or acetonitrile. The temperature at which the reaction is conducted is not critical and any temperature sufficient to produce Compound 1 may be employed. Temperatures of −45° C. to 50° C. are satisfactory, preferably about 0° C. to 40° C.

The examples illustrate the present invention without, however, limiting the same thereto. All temperatures are expressed in degrees Celsius.

EXAMPLE 1 p-Nitrobenzyl-2-diazoacetoacetate

A solution of 156 g of p-nitrobenzyl alcohol (94% purity) and 125.8 g methyl acetoacetate in 900 ml toluene was refluxed for 18 hours through a Soxlet extractor containing 100 g 4A molecular sieves. The sieves were replaced after 3 hours and 9 hours. The solutions were then cooled to 20° C. and 20.5 g triethyl amine were added, followed by a 200 ml solution of 387 g of p-dodecyl benzene sulfonylazide in heptanes over 0.5 hours. The reaction temperature was maintained at 25°–30° C. The solution was aged at 25° C. for 1.5 hours, then at 5° C. for 4 hours. The resulting mixture was filtered and the collected solid product was washed with 2×50 ml toluene and 2×100 ml heptanes. The product was then dried under vacuum to give 208 g of p-nitrobenzyl-2-diazoacetoacetate having a purity of 95% as measured by NMR.

EXAMPLE 2

(3S,4R)-4-(3-[(R)-1′-Hydroxyethyl]-4-azetidin-2-one)-3-diazo-2-oxo-butanoic acid p-nitrobenzyl ester Step A: 4-Nitrobenzyl-2-diazo-3-trimethyl silyloxy-3-butenoate.

27.7 g of p-nitrobenzyl 2-diazoacetoacetate (95% purity) and 17.5 g of sodium iodide was dissolved in 35 ml of acetonitrile under an nitrogen atmosphere. 11.7 g of triethylamine and 12.4 g of chlorotrimethyl silane were added consecutively and the exothermic reaction mixture warmed to 45° C. The reaction mixture was stirred for 0.5 hours, then diluted with 225 ml of toluene. 52 ml of the solvent was distilled off at 120 mm vacuum pressure and the mixture then stored at 5° C. for 1 hour. The mixture was then filtered through Celite under nitrogen atmosphere and the product-containing-filtrate diluted to give a total volume of 280 ml.

Step B: To the solution of the silyloxybutenoate from Step A above was added 25.7 g of (3S, 4R)-3-[(R)-1-t-butyldimethyl silyloxy-ethyl]-4-acetoxy azetidin-2-one and 2.84 g of anhydrous zinc bromide. The reaction mixture was stirred for 48 hours at ambient temperature. At the end of the reaction time, 30 ml methanol and 1.63 g of methanesulfonic acid were added and the mixture was stirred for 48 hours at 20° C. At the end of this 48 hours the solid product was filtered, washed with toluene and vacuum dried 6 hours at 40° C. to give 29.77 g of the title compound having 94% purity by NMR.

NMR (CDCl$_3$, TMS) δ1.3 (d, 3H); 1.9 (s,1H); 2.9 (dd, 1H); 3.2 (m, 2H); 4.0 (m, 1H); 4.2 (s,1H); 5.4 (s, 2H); 6.0 (s, 1H); 7.5 (d, 2H); 8.3 (d, 2H).

The subject matter which applicants regard as their invention is particularly pointed out and distinctly claimed as follows.

What is claimed is:

1. A process for the preparation of 2-diazo-3-trisubstituted silyloxy 3-butenoate ester of the Formula 1:

PROCESS FOR THE PREPARATION OF 2-DIAZO-3-TRISUBSTITUTED SILYLOXY 3-BUTENOATES

RELATED APPLICATION

This application is a continuation of U.S. Ser. No. 611,237, filed Nov. 9, 1990, now abandoned, which is a continuation-in-part of U.S. Ser. No. 381,344, filed Jul. 18, 1989, now abandoned.

BACKGROUND OF THE INVENTION

The instant invention relates to a novel process for preparing 2-diazo-3-trimethylsilyloxy-3-butenoates.

1-(4-Nitrobenzyl)-1-oxo-2-diazo-3-(trimethyl silyloxy) butene has been described (U.S. Pat. No. 4,525,582) as a synthon used in the conversion of 3-substituted-4-acetoxy azetidinones and penicillin to thienamycin.

A different process than this invention for preparing one of the silyloxy-3-butenoates, described as a key intermediate used in the synthesis of thienamycin and other carbapenem antibiotics, has been disclosed (U.S. Pat. No. 4,683,296) wherein a triflate silylating agent and a base were reacted with a p-nitrobenzyl diazoacetoacetate. This patent makes specific reference to the "use of weaker organic bases such as trialkylamines with the triorganic silyl halide silylating agent" which "does not produce the desired enol silyl ester" of this specific p-nitrobenzyl diazoacetoacetate.

The general reaction for converting simple nonfunctionalized ketones to silyl enol ethers has been previously described by Cazeau, et al. (*Tetrahedron*, 43, 2075–2088(1987)).

It is the object of the instant invention to provide a novel process for the preparation of diazosilyloxybutenoates which are useful in the synthesis of carbapenem antibiotic compounds.

DESCRIPTION OF THE INVENTION

Applicants now have discovered a practical and inexpensive process for the preparation of the silyloxy 3-butenoate having the Formula 1:

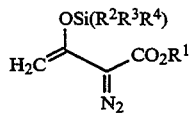

wherein $R^1$ is :
a) $C_1$–$C_6$ alkyl;
b) $C_1$–$C_6$ alkenyl;
c) phenyl substituted by 1–3 substituents which independently are: hydrogen, bromine, chlorine, fluorine, $C_1$–$C_4$ alkyl, $C_1$–$C_4$ alkoxy or nitro:
d) $C_1$–$C_4$ alkyl substituted by c) herein above; or
e) benzhydryl or triphenyl methyl; $R^2$, $R^3$, $R^4$ are independently:
f) $C_1$–$C_4$ alkyl;
g) phenyl substituted by 1–3 substituents which independently are: hydrogen, $C_1$–$C_4$ alkyl; or
h) —$OR^5$ where $R^5$, is f) or g) hereinabove;
WHICH COMPRISES the reaction of the compound of the Formula 2:

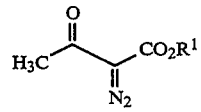

wherein $R^1$ is described hereinabove;
WITH 0.9 to 4.0 molar equivalents of a trisubstituted silyl halide of the Formula 3:

$$(R^2R^3R^4)SiX \qquad 3$$

wherein $R^2$, $R^3$, $R^4$ are described hereinabove and X is bromine or chlorine; IN THE PRESENCE of a base, selected from: diisopropyl ethyl amine, DBU (1,8-diazabicyclo-[5.4.0]-undec-7-ene), DBN (1,5-diazabicyclo-[4.3.0]-non5-ene) and tri($C_1$–$C_4$)alkylamines (e.g. trimethylamine, triethylamine, tributylamine, triisopropylamine); and a salt selected from: sodium iodide, potassium iodide and cesium iodide, both in an amount sufficient to produce compound 1, in a suitable organic solvent in an inert atmosphere and at a temperature sufficient to produce compound 1.

Alkyl, alkoxy, and alkenyl are intended to include linear and branched structures.

Alkyl, includes methyl, ethyl, propyl, isopropyl, butyl, sec- and tert- butyl and the like.

Alkenyl includes vinyl, allyl, isopropenyl, pentenyl, hexenyl and the like.

Alkoxy includes methoxy, ethoxy, propoxy, isopropoxy, butoxy and the like.

The trisubstituted silyl halide of formula 3 will hereafter be referred to as "triorganosilyl halide." The salt hereinabove will hereinafter be referred to as an "alkali metal iodide."

Preferably $R^1$ is: allyl, benzyl, benzhydryl, cinnamyl, p-bromobenzyl, p-methoxybenzyl, p-nitrobenzyl, o-nitrobenzyl, 2,4,6,-trimethylbenzyl or trityl.

Preferably $R^2$, $R^3$, $R^4$ are independently methyl, ethyl, isopropyl, t-butyl, phenyl and phenoxy.

Preferably 1.0 to 4.0 molar equivalents of the base and the salt are employed in the process.

Preferably the temperature is between −40° C. and 50° C.

More preferably 1.0 to 1.6 molar equivalents of the trisubstituted silyl halide, the base and the salt are employed in the process.

Most preferably $R^1$ is p-nitropbenzyl.

Most preferably $R^2$, $R^3$, $R^4$ are methyl.

Most preferably 1.1 molar equivalents of the trisubstituted silyl halide, the base and the salt are employed in the process.

The process of the instant invention whereby these results are obtained is illustrated in the following general reaction scheme. The scheme and subsequent description is illustrative and is not meant to be limiting.

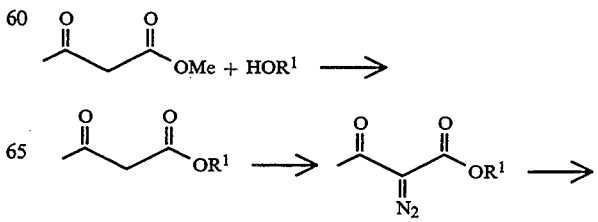

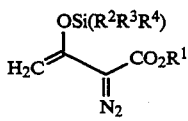

wherein R¹ is:
a) $C_1-C_6$ alkyl;
b) $C_2-C_6$ alkenyl;
c) phenyl optionally substituted by 1–3 substituents which independently are: bromine, fluorine, $C_1-C_4$ alkyl, $C_1-C_4$ alkoxy or nitro;
d) $C_1-C_4$ alkyl substituted by c) herein above;
e) benzhydryl or triphenylmethyl; $R^2$, $R^3$, $R^4$ are independently selected from:
f) $C_1-C_4$ alkyl;
g) phenyl optionally substituted by 1–3 substituents which independently are $C_1-C_4$ alkyl;
h) $-OR^5$ where $R^5$ is f) or g) hereinabove; which comprises the reaction of the diazoacetate of the Formula 2:

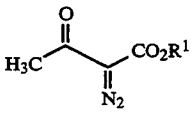

wherein $R_1$ is described hereinabove; and a trisubstituted silyl halide of the Formula 3:

$(R^2R^3R^4)SiX$  3 wherein $R^2$, $R^3$, $R^4$ are described hereinabove and X is bromine or chlorine; IN THE PRESENCE of a base, selected from: DBU (1, 8-diazabicyclo-[5.4.0]- undec-7-ene), DBN (1,5-diazabicyclo-[4.3.0]-non-5-ene) and tri($C_1-C_4$)alkylamine; and salt selected from: sodium iodide, potassium iodide and cesium iodide, both in a amount sufficient to produce compound 1;
with an aprotic organic solvent in an inert atmosphere and at a temperature sufficient to produce compound 1.

2. The process for the preparation of 2-diazo-3-trisubstituted silyloxy 3-butenoate ester of Formula 1:

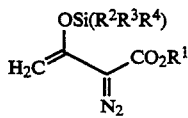

wherein R¹ is allyl, benzyl, benzhydryl, cinnamyl, p-bromobenzyl, p-methoxybenzyl, p-nitrobenzyl, o-nitrobenzyl, 2,4,6-trimethylbenzyl or triphenylmethyl; $R^2$, $R^3$, $R^4$ are independently $C_1-C_4$ alkyl; which comprises the reaction of the diazoacetate of the Formula 2:

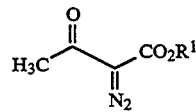

and a trisubstituted silyl chloride of the Formula 3:

$(R^2R^3R^4)SiCl$  3 wherein $R^2$, $R^3$, $R^4$ are described hereinabove; with a base which is a tri($C_1-C_4$ alkyl) amine; and a salt which is potassium iodide or sodium iodide both in an amount sufficient to produce compound 1, in an aprotic organic solvent in an inert atmosphere.

3. A method for producing a compound of the formula:

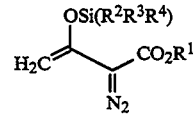

in which R¹ is $C_1-C_6$ alkyl; phenyl optionally substituted by 1–3 substituents which independently are bromine, fluorine, $C_1-C_4$alkyl, $C_1-C_4$ alkoxy or nitro; phenyl $C_1-C_4$alkyl; or allyl; and $R^{2-4}$ which may or may not be the same are $C_1-C_4$ alkyls by allowing the compound represented by the formula,

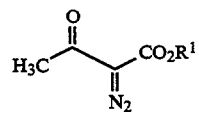

to react with a compound represented by the formula,

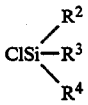

$R^{1-4}$ in the formulae being as defined above, in a suitable aprotic organic solvent in the presence of the base selected from DBU, DBN and tri-($C_1-C_4$)alkylamines and alkali metal halide represented by:

MI which M is a sodium, potassium or cesium.

4. The process of claim 1 wherein R¹ is $C_2-C_4$ alkenyl or $C_1-C_4$ alkyl substituted by phenyl which is substituted by: hydrogen, bromine, $C_1-C_4$alkyl, $C_1-C_4$ alkoxy, or nitro; $R^2$, $R^3$, $R^4$ are independently $C_1-C_4$ alkyl, phenyl or phenoxy.

5. The process of claim 2 wherein R¹ is p-methoxybenzyl or p-nitrobenzyl and $R^2$, $R^3$, $R^4$ are independently selected from methyl, ethyl or t-butyl.

6. The process of claim 2 wherein R¹ is p-nitrobenzyl and $R^2$, $R^3$, $R^4$ are each methyl and the base is triethylamine.

7. The process of claim 2 wherein aprotic organic solvent is acetonitrile or a mixture of acetonitrile and toluene.

* * * * *